(12) United States Patent
Richter et al.

(10) Patent No.: US 11,799,048 B2
(45) Date of Patent: Oct. 24, 2023

(54) OPTOELECTRONIC SENSOR

(71) Applicant: OSRAM Opto Semiconductors GmbH, Regensburg (DE)

(72) Inventors: Daniel Richter, Bad Abbach (DE); Luca Haiberger, Regensburg (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 319 days.

(21) Appl. No.: 17/274,312

(22) PCT Filed: Oct. 8, 2019

(86) PCT No.: PCT/EP2019/077195
§ 371 (c)(1),
(2) Date: Mar. 8, 2021

(87) PCT Pub. No.: WO2020/074497
PCT Pub. Date: Apr. 16, 2020

(65) Prior Publication Data
US 2021/0328089 A1    Oct. 21, 2021

(30) Foreign Application Priority Data
Oct. 10, 2018 (DE) .......................... 102018125050.9

(51) Int. Cl.
*H01L 31/173* (2006.01)
*A61B 5/00* (2006.01)
(Continued)

(52) U.S. Cl.
CPC .......... *H01L 31/173* (2013.01); *A61B 5/0059* (2013.01); *H01L 31/0203* (2013.01); *H01L 31/02164* (2013.01); *H01L 31/02165* (2013.01)

(58) Field of Classification Search
None
See application file for complete search history.

(56) References Cited

U.S. PATENT DOCUMENTS 7,604,981 B1    10/2009 Harris, Jr. et al.
2013/0327931 A1    12/2013 Hsu et al.
(Continued)

FOREIGN PATENT DOCUMENTS

EP    1670105 A1    6/2006
JP    2005156549 A    6/2005
(Continued)

*Primary Examiner* — Evren Seven
(74) *Attorney, Agent, or Firm* — Slater Matsil, LLP

(57) ABSTRACT

In an embodiment an optoelectronic sensor includes a radiation-emitting semiconductor region, a radiation-detecting semiconductor region, a first polarization filter arranged above the radiation-emitting semiconductor region and including a first polarization direction and a second polarization filter arranged above the radiation-detecting semiconductor region and including a second polarization direction, wherein the first polarization direction and the second polarization direction are perpendicular to each other, wherein a radiation-reflecting or radiation-absorbing layer is arranged on side flanks of the radiation-emitting semiconductor region and/or the radiation-detecting semiconductor region and/or the first polarization filter and/or the second polarization filter.

14 Claims, 3 Drawing Sheets

(51) Int. Cl.
*H01L 31/0203* (2014.01)
*H01L 31/0216* (2014.01)

(56) References Cited

U.S. PATENT DOCUMENTS

| | | | |
|---|---|---|---|
| 2013/0334544 A1* | 12/2013 | Luruthudass | H01L 31/147 257/82 |
| 2016/0013223 A1 | 1/2016 | Chang et al. | |
| 2016/0061653 A1 | 3/2016 | Chang et al. | |
| 2017/0172476 A1 | 6/2017 | Schilthuizen | |
| 2017/0356982 A1 | 12/2017 | Buettgen et al. | |

FOREIGN PATENT DOCUMENTS

| | | |
|---|---|---|
| WO | 2017080869 A1 | 5/2017 |
| WO | 2018162732 A1 | 9/2018 |

\* cited by examiner

OPTOELECTRONIC SENSOR

This patent application is a national phase filing under section 371 of PCT/EP2019/077195, filed Oct. 8, 2019, which claims the priority of German patent application 102018125050.9, filed Oct. 10, 2018, each of which is incorporated herein by reference in its entirety.

TECHNICAL FIELD

This application relates to an optoelectronic sensor, in particular an optoelectronic sensor for measuring a vital parameter in a wearable device.

BACKGROUND

Monitoring of vital parameters by an optoelectronic sensor in a wearable device, for example in a sports watch, requires a particularly compact sensor with high sensitivity.

SUMMARY OF THE INVENTION

Embodiments provide an optoelectronic sensor that has a compact design and a high sensitivity.

According to at least one embodiment, the optoelectronic sensor comprises a radiation-emitting semiconductor region and a radiation-detecting semiconductor region. The radiation-emitting semiconductor region comprises, in particular, an active layer suitable for emitting radiation. The active layer can be formed, for example, as a pn junction, a double heterostructure, a single quantum well structure or a multiple quantum well structure. The term quantum well structure includes any structure in which charge carriers undergo quantization of their energy states by confinement. In particular, the term quantum well structure does not contain any indication of the dimensionality of the quantization. Thus, it includes inter alia quantum wells, quantum wires, and quantum dots, and any combination of these structures.

In particular, the radiation-detecting semiconductor region comprises an active layer suitable for detecting radiation, such as a photodiode or other semiconductor layer sequence suitable for detecting radiation.

According to at least one embodiment, the optoelectronic sensor comprises a first polarization filter arranged above the radiation-emitting semiconductor region and a second polarization filter arranged above the radiation-detecting semiconductor region. In particular, the first polarization filter may be arranged directly on a radiation exit surface of the radiation-emitting semiconductor region. Similarly, the second polarization filter may be directly arranged on the radiation entrance surface of the radiation-detecting semiconductor region. Arranging the polarization filters directly on the semiconductor regions, for example in the form of a layer or a layer sequence, advantageously contributes to a compact structure of the optoelectronic sensor.

The first polarization filter comprises a first polarization direction and the second polarization filter comprises a second polarization direction. Here, the first polarization direction is different from the second polarization direction, in particular, the first polarization direction and the second polarization direction are perpendicular to each other. For example, the first polarization filter arranged above the radiation-emitting semiconductor region generates linearly polarized radiation having the first polarization direction, and the second polarization filter arranged above the radiation-detecting semiconductor region generates linearly polarized radiation having a second polarization direction that is perpendicular to the first polarization direction. In other words, the first and second polarization filters form crossed polarizers.

By the first and second polarization filters comprising polarization directions oriented perpendicular to each other, it is advantageously achieved that the radiation emitted from the radiation-emitting semiconductor region exits the optoelectronic sensor with a polarization direction for which the second polarization filter above the radiation-detecting semiconductor region is substantially nontransmissive.

In particular, the radiation emitted from the radiation-detecting semiconductor region is provided as excitation light for measuring a vital parameter. The emitted radiation may be at least partially absorbed and/or reflected by a body region, such as tissue or blood vessels. The radiation-detecting semiconductor region is particularly provided for detecting the radiation emitted from the body region as a result of the excitation. In particular, the detected radiation may be used to detect one or more vital signs such as blood pressure and/or heart rate. The detected radiation typically comprises lower energy radiation, i.e., radiation of a longer wavelength. Furthermore, the radiation to be detected typically comprises very low intensity compared to the intensity of the excitation light. Due to the fact that the excitation light generated by the radiation-emitting semiconductor region is substantially not transmitted by the second polarization filter because of its polarization direction, the excitation light is advantageously separated from the radiation to be detected from the body region before reaching the radiation-detecting semiconductor region.

Therefore, the light emitted from the radiation-emitting semiconductor region contributes very little to the signal light detected by the radiation-detecting semiconductor region. In this way, a high sensitivity of the optoelectronic sensor is advantageously achieved.

According to at least one embodiment of the optoelectronic sensor, the radiation-detecting semiconductor region is arranged laterally next to the radiation-emitting semiconductor region. In this way, the space required for the optoelectronic sensor is kept small.

According to at least one embodiment of the optoelectronic sensor, the radiation exit surface of the radiation-emitting semiconductor region and the radiation entrance surface of the radiation-detecting semiconductor region are arranged parallel to each other.

In particular, the radiation-emitting semiconductor region and the radiation-detecting semiconductor region are arranged such that a main emission direction of the radiation-emitting semiconductor region and a main incidence direction of the radiation-detecting semiconductor region are substantially anti-parallel to each other.

According to at least one embodiment of the optoelectronic sensor, the radiation-emitting semiconductor region and the radiation-detecting semiconductor region are arranged on a common carrier. The common carrier may comprise, for example, electrical contacts for contacting the radiation-emitting semiconductor region and the radiation-detecting semiconductor region.

According to at least one embodiment of the optoelectronic sensor, the radiation-emitting semiconductor region and the radiation-detecting semiconductor region are monolithically integrated. "Monolithically integrated" means, in particular, that the radiation-emitting semiconductor region and the radiation-detecting semiconductor region comprise a common growth substrate. In particular, the radiation-emitting semiconductor region and the radiation-detecting semiconductor region may be epitaxially grown on the common growth substrate. It is possible that the radiation-emitting semiconductor region and the radiation-detecting semiconductor region comprise, at least in some regions, semiconductor layers grown in the same epitaxial growth process. The radiation-emitting semiconductor region and/or the radiation-detecting semiconductor region may comprise, in particular, a mesa structure. Thus, the lateral extent of the semiconductor layer sequence is smaller than the lateral extent of a supporting substrate such as the growth substrate. The mesa structure may be fabricated by a photolithographic process in which the semiconductor layer sequence is partially ablated to pattern it to a desired shape and size.

According to at least one embodiment of the optoelectronic sensor, a distance between the radiation-emitting semiconductor region and the radiation-detecting semiconductor region is not more than 150 μm. Here, the "distance" means the shortest distance between the radiation-emitting semiconductor region and the radiation-detecting semiconductor region, i.e., the width of the gap between the radiation-emitting semiconductor region and the radiation-detecting semiconductor region. Preferably, the distance is at least 20 μm to reduce optical crosstalk. Thus, the distance between the radiation-emitting semiconductor region and the radiation-detecting semiconductor region is preferably between 20 μm and 150 μm.

According to at least one embodiment of the optoelectronic sensor, a radiation-reflecting or radiation-absorbing layer is applied to side flanks of the radiation-emitting semiconductor region and/or the radiation-detecting semiconductor region. Preferably, both the side flanks of the radiation-emitting semiconductor region and the side flanks of the radiation-detecting semiconductor region are covered with the radiation-reflecting or radiation-absorbing layer. In this way, optical crosstalk between the radiation-emitting semiconductor region and the radiation-detecting semiconductor region can be further reduced. The radiation-reflecting or radiation-absorbing layer is preferably a dielectric layer or layer sequence. Alternatively or additionally, the side flanks of the first polarization filter and/or the side flanks of the second polarization filter may be covered by the radiation-reflecting or radiation-absorbing layer.

According to at least one embodiment of the optoelectronic sensor, the first polarization filter and/or the second polarization filter is an absorbing polarization filter. In an absorbing polarization filter, light with the pass polarization direction is transmitted and other polarization directions are absorbed within the polarization filter. In this embodiment, the first and/or second polarization filter may comprise, for example, herapathite.

According to at least one embodiment of the optoelectronic sensor, the first polarization filter and/or the second polarization filter is a reflective polarization filter.

In a reflective polarization filter, light with the pass polarization direction is transmitted and other polarization directions are reflected. In this embodiment, the first and/or second polarization filter may comprise, for example, a dielectric layer sequence.

According to at least one embodiment of the optoelectronic sensor, the radiation-emitting semiconductor region and the radiation-detecting semiconductor region are surrounded in the lateral direction by a plastic molding compound comprising, for example, silicone or epoxy resin. The plastic molding compound can be applied by injection molding, transfer molding, or compression molding, for example. The plastic molding compound is advantageously opaque, i.e., in particular, not transparent to the emitted radiation. Preferably, the plastic molding compound contains radiation-absorbing and/or radiation-reflecting particles. In this way, the crosstalk between the radiation-emitting semiconductor region and the radiation-detecting semiconductor region can be further reduced. Alternatively or additionally, the side flanks of the first polarization filter and/or the side flanks of the second polarization filter may be covered by the plastic molding compound.

According to at least one embodiment, the optoelectronic component is a surface mounted device (SMD). In this embodiment, in particular the electrical contacts are arranged on a back side facing away from the radiation exit surface and radiation entrance surface, so that the component can be mounted on the back side, for example on a printed circuit board. In this case, the front side of the optoelectronic sensor is advantageously free of electrical leads such as bonding wires, so that absorption of the emitted light or the light to be detected by electrical leads is avoided.

According to at least one embodiment of the optoelectronic sensor, the radiation-emitting semiconductor region is suitable for emitting infrared radiation and the radiation-detecting semiconductor region is suitable for detecting infrared radiation. In this embodiment, the radiation-emitting semiconductor region and the radiation-detecting semiconductor region may be based on an arsenide compound semiconductor, for example. "Based on an arsenide compound semiconductor" in the present context means that the active epitaxial layer sequence, or at least one layer thereof, comprises an arsenide compound semiconductor material, preferably $Al_nGa_mIn_{1-n-m}As$, wherein $0 \leq n \leq 1$, $0 \leq m \leq 1$ and $n+m \leq 1$. This material need not necessarily comprise a mathematically exact composition according to the above formula. Rather, it may comprise one or more dopants as well as additional constituents. For the sake of simplicity, however, the above formula includes only the essential constituents of the crystal lattice (Al, Ga, In, As), even if these may be partially replaced by small amounts of other substances. Alternatively, however, it is also possible for the radiation-emitting semiconductor region and/or the radiation-detecting semiconductor region to be based on a different semiconductor material, in particular on a III-V semiconductor material.

The optoelectronic sensor may in particular be configured to measure at least one vital parameter. A vital parameter is a measure that reflects a basic function of the human body. Such a vital parameter may be, for example, the heart rate or the blood pressure or the oxygen content in the blood.

According to at least one embodiment, the optoelectronic sensor is part of a wearable device, in particular a wearable device for measuring a vital parameter such as, for example, a sports watch or a fitness wristband. The compact design of the optoelectronic sensor is particularly advantageous for the integration of the optoelectronic sensor into such a device.

BRIEF DESCRIPTION OF THE DRAWINGS

The invention is explained in more detail below by means of exemplary embodiments in connection with FIGS. 1 to 6.

Components that are the same or have the same effect are each given the same reference signs in the figures. The components shown as well as the proportions of the components among each other are not to be regarded as true to scale.

DETAILED DESCRIPTION OF ILLUSTRATIVE EMBODIMENTS

Figure 1:
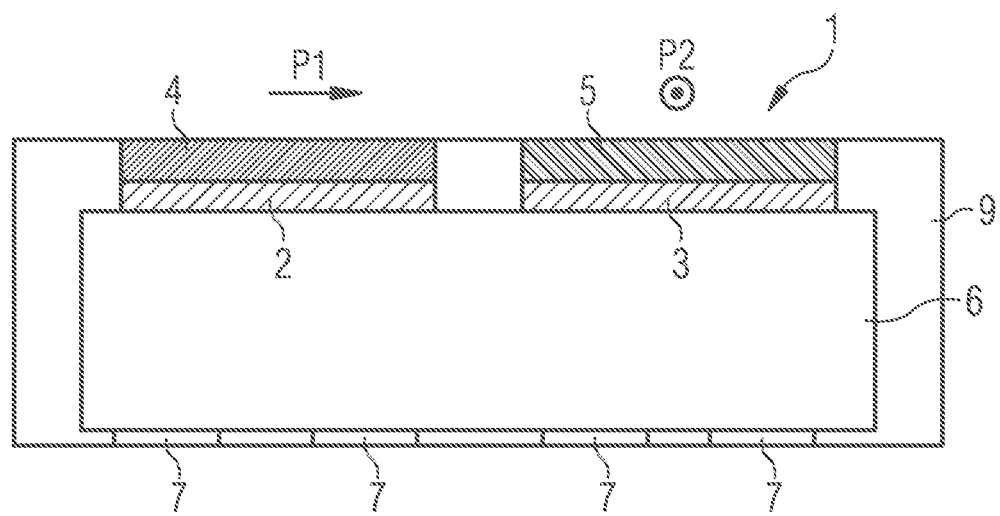
FIG. 1 shows a schematic representation of a cross-section through an optoelectronic sensor according to a first exemplary embodiment.

FIG. 1 schematically shows a first exemplary embodiment of the optoelectronic sensor in cross-section. The optoelectronic sensor 1 comprises a radiation-emitting semiconductor region 2 and a radiation-detecting semiconductor region 3. The radiation-emitting semiconductor region 2 and the radiation-detecting semiconductor region 3 are each formed by a semiconductor layer sequence whose individual layers are not shown here.

For example, the radiation-emitting semiconductor region 2 and the radiation-detecting semiconductor region 3 may each comprise a semiconductor layer sequence based on a III-V semiconductor material, such as a semiconductor layer sequence based on an arsenide compound semiconductor material. In particular, the radiation-emitting semiconductor region 2 may comprise a light-emitting diode layer sequence. The radiation-detecting semiconductor region 3 may be a photodiode, for example.

The radiation-emitting semiconductor region 2 and the radiation-detecting semiconductor region 3 are arranged laterally adjacent to each other such that a radiation exit surface of the radiation-emitting semiconductor region and a radiation entrance surface of the radiation-detecting semiconductor region are arranged parallel to each other, in particular in a plane.

The radiation-emitting semiconductor region 2 and the radiation-detecting semiconductor region 3 are arranged on a common carrier 6. The common carrier 6 may in particular be a common growth substrate. In other words, the radiation-emitting semiconductor region 2 and the radiation-detecting semiconductor region 3 are monolithically integrated. In particular, the semiconductor layer sequences of the radiation-emitting semiconductor region 2 and the radiation-detecting semiconductor region 3 may be epitaxially grown on the common growth substrate. The radiation-emitting semiconductor region 2 and the radiation-detecting semiconductor region 3 comprise, in particular, a mesa structure that can be produced, for example, by an etching process.

Alternatively, it is also possible that the radiation-emitting semiconductor region 2 and the radiation-detecting semiconductor region 3 are separately fabricated semiconductor chips that are connected to the common carrier 6 by means of a bonding layer such as a solder layer. In this embodiment, the radiation-emitting semiconductor region 2 and the radiation-detecting semiconductor region 3 may be, in particular, so-called thin-film semiconductor bodies. In the production of a thin-film semiconductor body, a functional semiconductor layer sequence, which in particular comprises the active layer, is first epitaxially grown on a growth substrate, then the carrier 6 is applied on the surface of the semiconductor layer sequence opposite the growth substrate, and subsequently the growth substrate is separated. Since the growth substrates used for nitride compound semiconductors, for example SiC, sapphire or GaN, are comparatively expensive, this method offers the advantage that the growth substrate can be recycled. The detachment of a growth substrate made of sapphire from a semiconductor layer sequence made of a nitride compound semiconductor can, for example, be carried out using a laser lift-off method.

The common carrier 6 comprises electrodes 7 on the back side for electrically contacting the radiation-emitting semiconductor region 2 and the radiation-detecting semiconductor region 3. The electrical connections between the electrodes 7 and the radiation-emitting semiconductor region 2 and the radiation-detecting semiconductor region 3 are not shown in detail here for convenience. It is possible, for example, that these connections are realized by way of vias through the carrier 6. The common carrier 6 may be, for example, a silicon substrate or a glass substrate.

The optoelectronic sensor 1 is in particular a surface mountable component. In particular, the optoelectronic sensor can be mounted on a printed circuit board by means of electrodes 7 arranged on the back side of the carrier 6. The optoelectronic sensor 1 can be connected at the electrodes in particular to a control unit which is configured to control the optoelectronic sensor and to evaluate the signal.

In the case of the optoelectronic sensor 1, a first polarization filter 4 is arranged above the radiation-emitting semiconductor region 2. In the exemplary embodiment, the first polarization filter 4 is a radiation-absorbing polarization filter, which transmits radiation of only one polarization direction P1 from the emitted radiation and absorbs other polarization directions. The first polarization filter 4 can generate, in particular, linearly polarized radiation with the polarization direction P1 from the emitted radiation. For example, the first polarization direction P1 is oriented parallel to the drawing plane.

Furthermore, a second polarization filter 5 is arranged above the radiation-detecting semiconductor region 3. In the exemplary embodiment, the second polarization filter 5 is a radiation-absorbing polarization filter which only transmits radiation of a second polarization direction P2 and absorbs other polarization directions. The second polarization filter 5 may comprise, for example, a transmission direction for linearly polarized radiation with the polarization direction P2. The second polarization direction P2 is oriented perpendicular to the drawing plane, for example.

The first polarization filter 4 is advantageously arranged directly on the radiation-emitting semiconductor region 2, and the second polarization filter 5 is advantageously arranged directly on the radiation-detecting semiconductor region 3. The first polarization filter 4 and the second polarization filter 5 may be, for example, polarizing crystal platelets attached to the radiation-emitting semiconductor region 2 and to the radiation-detecting semiconductor region 3 by means of a bonding layer such as an adhesive.

The first polarization filter 4 and/or the second polarization filter 5 may comprise, for example, herapathite.

The polarization direction P2 of the second polarization filter 5 is perpendicular to the polarization direction P1 of the first polarization filter 4, so the polarization directions P1 and P2 are crossed. In this way, it is advantageously achieved that radiation emitted from the radiation-emitting semiconductor region 2 which has passed the first polarization filter 4 is not transmitted by the polarization filter 5 above the radiation-detecting semiconductor region 3. In this way, the radiation-detecting semiconductor region 3 is shielded from the emitted radiation to the greatest extent possible. In other words, crosstalk between the radiation-emitting semiconductor region 2 and the radiation-detecting semiconductor region 3 is reduced. In this way, the sensitivity of the radiation-detecting semiconductor region 3 to a signal radiation, which may be unpolarized in particular, is advantageously increased compared to the sensitivity to the emitted radiation. In particular, the signal-to-noise ratio of the detector signal is improved in this way.

The radiation-emitting semiconductor region 2 and the radiation-detecting semiconductor region 3 are laterally surrounded by a plastic molding compound 9. The plastic molding compound 9 is advantageously opaque. In the exemplary embodiment, the plastic molding compound 9 is an opaque plastic molding compound that laterally surrounds the radiation-emitting semiconductor region 2, the first polarization filter 4, the radiation-detecting semiconductor region 3, the second polarization filter 5, and the common carrier 6. In particular, the opaque plastic molding compound 9 may comprise a matrix material having radiation-reflecting or radiation-absorbing particles embedded therein. The matrix material may be, for example, a silicone or an epoxy resin, and the particles may be, for example, $TiO_2$ particles. The opaque plastic molding compound 9 may be applied, for example, by injection molding, transfer molding, or compression molding. On the one hand, the plastic molding compound 9 serves to protect the optoelectronic sensor 1 from external influences, for example to protect it from mechanical damage, dirt or moisture. In addition, the fact that the plastic molding compound 9 is opaque further reduces crosstalk between the radiation-emitting semiconductor region 2 and the radiation-detecting semiconductor region 3.

Figure 2:
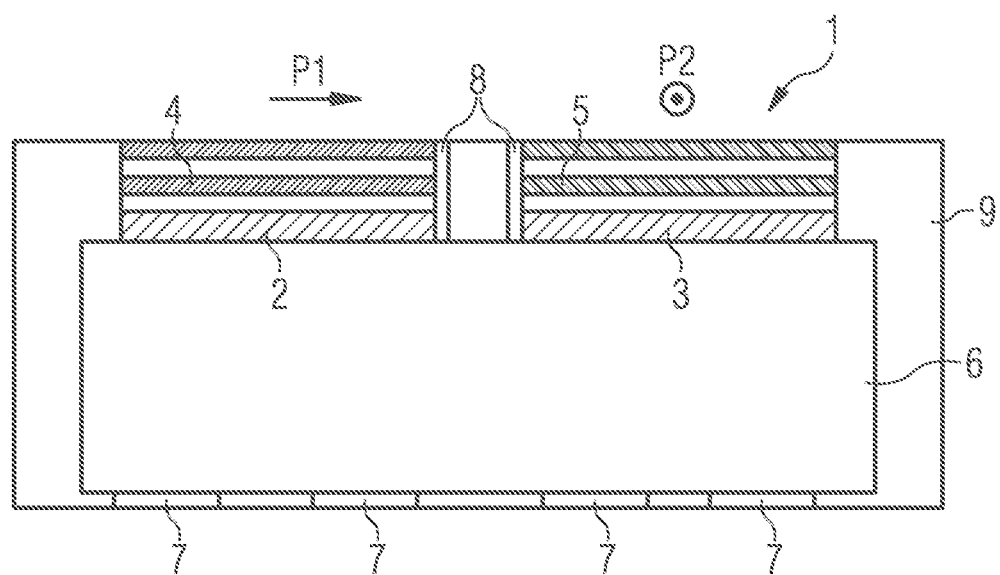
FIG. 2 shows a schematic representation of a cross-section through an optoelectronic sensor according to a further exemplary embodiment.

FIG. 2 illustrates a second exemplary embodiment of the optoelectronic sensor 1. The structure of the optoelectronic sensor 1 is substantially the same as that of the first exemplary embodiment. One difference from the first exemplary embodiment is that the first polarization filter 4 and the second polarization filter 5 are designed as reflective polarization filters. The first polarization filter 4, which is arranged on the radiation-emitting semiconductor region 2, is designed to transmit portions of radiation emitted with a first polarization direction P1 and to reflect back other portions of radiation.

In an analogous manner, the second polarization filter 5, which is arranged on the radiation-detecting semiconductor region 3, can also be designed as a reflective polarization filter. In this case, the radiation-detecting polarization filter 5 is configured to transmit portions of radiation of an incident signal light having the second polarization direction P2 and reflect back other portions of radiation.

The first polarization filter 4 and the second polarization filter 5 may comprise a polarizing layer or layer sequence, in particular a dielectric layer sequence. In particular, the first polarization filter 4 and the second polarization filter 5 may be dielectric interference layer systems.

The reflective property of the first polarization filter 4 and/or the second polarization filter 5 has the advantage of enabling so-called light recycling. This means that, for example, radiation which has entered the radiation-detecting semiconductor region 3 can be reflected once or several times between the reflective polarization filter 5 and the back side of the radiation-detecting semiconductor region 3 facing the carrier 6, until finally absorption takes place in the light-sensitive active layer of the radiation-detecting semiconductor region 3. Such radiation, which has not yet been absorbed after passing through the active layer once, is thus not lost, but can still be absorbed after being reflected once or several times, thus contributing to the detector signal.

In an analogous manner, for example, photons which have not yet been transmitted when first hitting the reflective polarization filter 4 of the radiation-emitting semiconductor region 2 may possibly be transmitted after being reflected once or several times in the radiation-emitting semiconductor region 2 and thus contribute to the emitted radiation.

A further difference between the second exemplary embodiment according to FIG. 2 and the first exemplary embodiment is that side flanks of the radiation-emitting semiconductor region 2 and the radiation-detecting semiconductor region 3 are each provided with a radiation-reflecting or radiation-absorbing layer 8. In particular, the facing side flanks of the radiation-emitting semiconductor region and the radiation-detecting semiconductor region 3 may be provided with the radiation-reflecting or radiation-absorbing layer 8. In addition, it is also possible that the side flanks of the radiation-emitting semiconductor region 2 and the radiation-detecting semiconductor region 3 facing away from each other are also covered with the radiation-absorbing layer 8. In particular, the radiation-reflecting or radiation-absorbing layer 8 may also cover the side flanks of the first polarization filter 4 and the second polarization filter 5. The radiation-reflecting or radiation-absorbing layer 8 further reduces crosstalk between the radiation-emitting semiconductor region 2 and the radiation-detecting semiconductor region 3.

Figure 3:
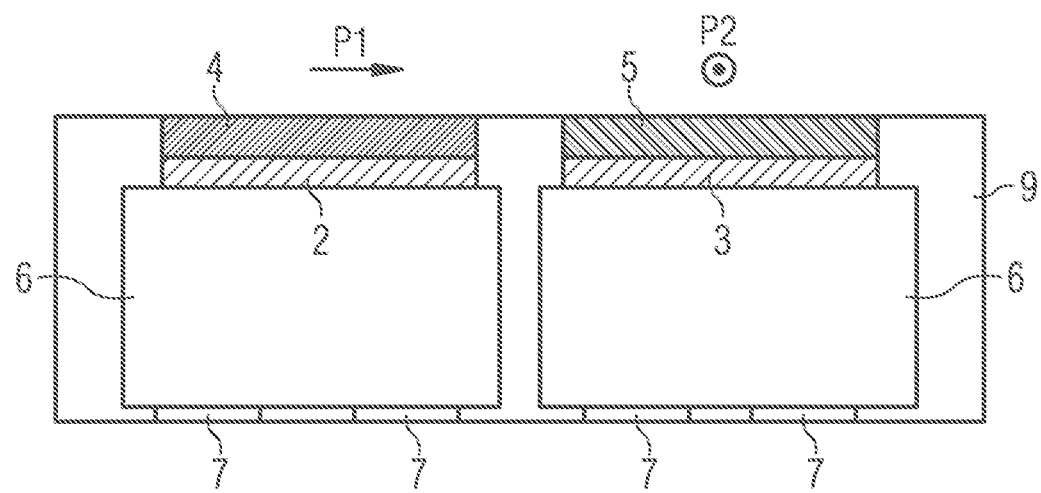
FIG. 3 shows a schematic representation of a cross-section through an optoelectronic sensor according to a further exemplary embodiment.

FIG. 3 illustrates a third exemplary embodiment of the optoelectronic sensor 1. The third exemplary embodiment differs from the first exemplary embodiment in that the radiation-emitting semiconductor region 2 and the radiation-detecting semiconductor region 3 do not comprise a common carrier 6, but separate carriers. Rather, in this exemplary embodiment, the radiation-emitting semiconductor region 2 and the radiation-detecting semiconductor region 3 are each part of a separate semiconductor chip. Nevertheless, the radiation-emitting semiconductor region 2 and the radiation-detecting semiconductor region 3 are also arranged next to each other at a small distance in this exemplary embodiment, preferably at a distance of at least 20 μm and at most 150 μm. The two semiconductor chips each comprise electrodes on the back side, so that advantageously both semiconductor chips arranged side by side are each surface-mountable semiconductor chips.

The radiation-emitting semiconductor region 2 and the radiation-detecting semiconductor region 3 are surrounded by a radiation-nontransmissive plastic molding compound 9, as in the previous examples. Advantageously, the plastic molding compound 9 is a plastic molding compound that connects the two adjacent semiconductor chips together to form a one-piece optoelectronic sensor 1. In particular, the space between the two adjacent semiconductor chips may be filled by the plastic molding compound 9. On the one hand, the plastic molding compound 9 represents the connecting member between the two semiconductor chips. Furthermore, the plastic molding compound 9 is advantageously opaque, so that optical crosstalk between the radiation-emitting semiconductor region 2 and the radiation-detecting semiconductor region 3 is reduced. With regard to further possible embodiments and the advantages resulting therefrom, the third exemplary embodiment otherwise corresponds to the first exemplary embodiment.

Figure 4:
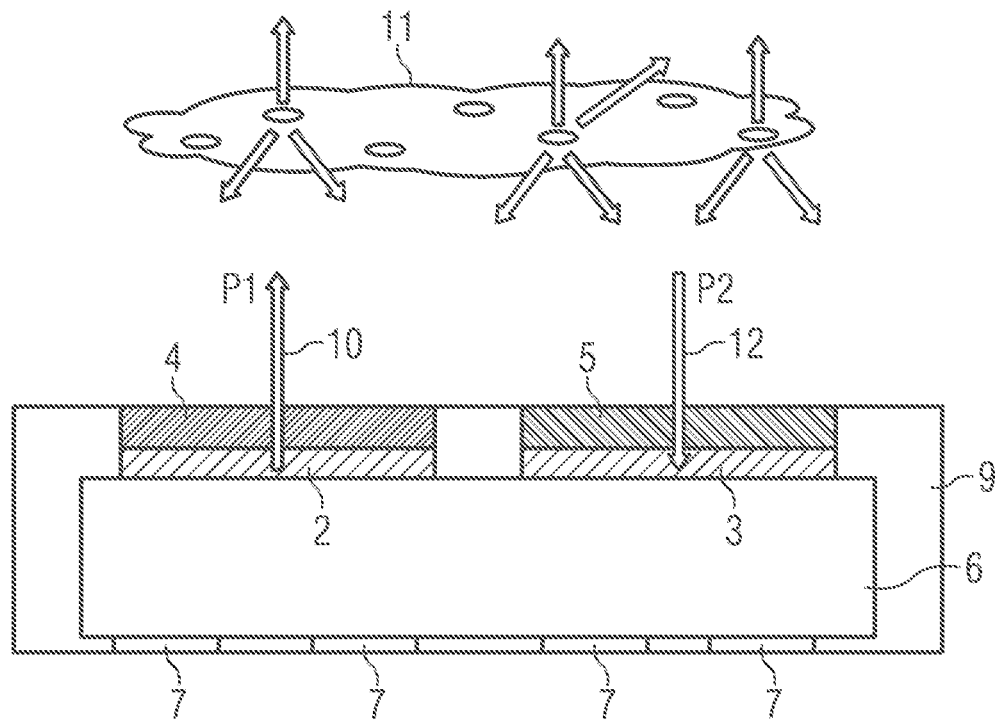
FIG. 4 shows a schematic representation of the beam path in an exemplary embodiment of the optoelectronic sensor.

FIG. 4 schematically illustrates a cross-section through an optoelectronic sensor 1 in an application intended for the optoelectronic sensor 1. The optoelectronic sensor 1 is configured as in the first exemplary embodiment. Alternatively, however, it would also be possible for the optoelectronic sensor 1 to be configured, for example, as in one of the exemplary embodiments of FIG. 2 or 3. In a method of operating the optoelectronic sensor 1, the radiation-emitting semiconductor region 2 emits radiation 10 in a main radiation direction that is perpendicular to a main surface of the optoelectronic sensor 1. The emitted radiation 10 passes through the first polarization filter 4 and is then advantageously linearly polarized.

The emitted radiation 10 can be absorbed as excitation light by an object 11, where it can excite the emission of a signal radiation 12, a part of which is detected by the radiation-detecting semiconductor region 3.

The signal radiation 12 reemitted after absorption typically comprises a lower energy and thus a longer wavelength than the emitted radiation 10. The object 11 may be, for example, human tissue. It is also possible that the object is liquid or gaseous, for example a drop of sweat or a gas excreted by the body can be examined.

Figure 5:
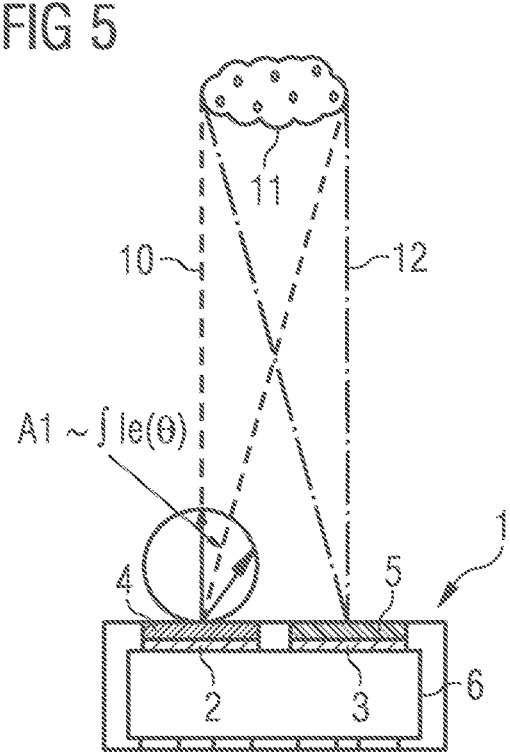
FIG. 5 shows a schematic representation of the beam path in an optoelectronic sensor with a small distance between the radiation-emitting semiconductor region and the radiation-detecting semiconductor region.

FIG. 5 schematically shows the beam path in an optoelectronic sensor 1 with a small distance between the radiation-emitting semiconductor region and the radiation-detecting semiconductor region. The small distance is achieved in particular by arranging the radiation-emitting semiconductor region 2 and the radiation-detecting semiconductor region 3 next to each other on a common carrier 6, wherein the distance is advantageously not more than 150 µm, in particular between 20 µm and 150 µm. The emitted radiation 10 impinges on the object 11 at different angles Θ. Similarly, the signal radiation 12 also impinges on the radiation-detecting semiconductor region 3 at different angles Θ. The radiation characteristic of the emitted radiation 10 can, for example, approximately correspond to the beam characteristic of a Lambert radiator. In this case, the radiant intensity Ie of the emitted light is at least approximately proportional to the cosine of the angle Θ, wherein Θ=0° denotes the main radiation direction, thus $I_e(\Theta)=I_o \cos \Theta$ holds. Here, $I_e(\Theta)$ is the radiant intensity at angle Θ to the main radiation direction and Io is the radiant intensity present in the main radiation direction (Θ=0°).

The radiant energy A1 incident on the object under examination is proportional to the integral of the radiant intensity $I_e(\Theta)$ over the angles Θ at which the radiation strikes the object. Since, at least approximately, $I_e(\Theta)=I_o \cos \Theta$ applies, the smaller the angles Θ relative to the main radiation direction, the greater the radiant intensity.

Figure 6:
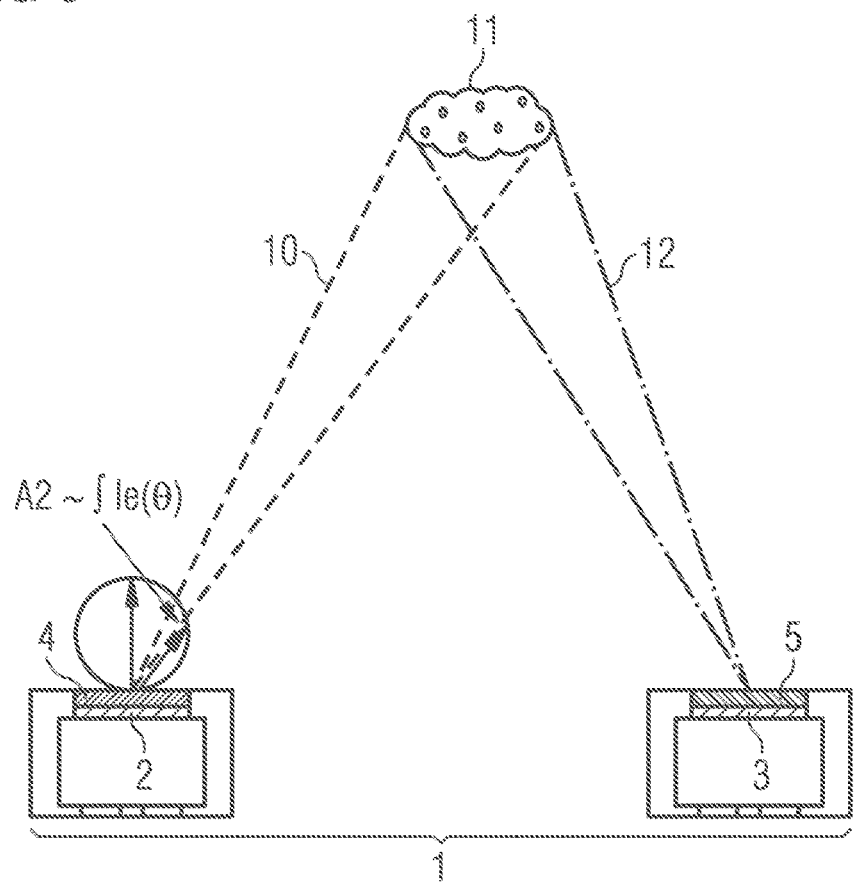
FIG. 6 shows a schematic representation of the beam path in an optoelectronic sensor with a large distance between the radiation-emitting semiconductor region and the radiation-detecting semiconductor region.

For comparison, FIG. 6 schematically shows the beam path in an optoelectronic sensor 1 with a greater distance between the radiation-emitting semiconductor region 2 and the radiation-detecting 3 semiconductor region. In this example, the greater distance is based in particular on the fact that the radiation-emitting semiconductor region 2 and the radiation-detecting semiconductor region 3 are separate semiconductor chips that are not arranged directly next to each other on a common carrier. In this case, the angles Θ relative to the main radiation direction are larger than in the example of FIG. 5, and therefore the radiant energy A2 incident on the object under examination is smaller than in the example of FIG. 5. Thus, it can be seen that arranging the radiation-emitting semiconductor region 2 and the radiation-detecting semiconductor region 3 side by side on a common carrier as shown in FIG. 5 is more advantageous.

The invention is not limited by the description based on the exemplary embodiments. Rather, the invention encompasses any new feature as well as any combination of features, which in particular includes any combination of features in the claims, even if that feature or combination itself is not explicitly specified in the claims or exemplary embodiments.

The invention claimed is:

1. An optoelectronic sensor comprising:
a radiation-emitting semiconductor region;
a radiation-detecting semiconductor region,
wherein the radiation-emitting semiconductor region and the radiation-detecting semiconductor region are monolithically integrated and arranged on a common growth substrate;
a first polarization filter arranged above the radiation-emitting semiconductor region and comprising a first polarization direction;
a second polarization filter arranged above the radiation-detecting semiconductor region and comprising a second polarization direction,
wherein the first polarization direction and the second polarization direction are perpendicular to each other; and
a radiation-reflecting or radiation-absorbing layer applied to side flanks of the radiation-emitting semiconductor region and/or the radiation-detecting semiconductor region and/or the first polarization filter and/or the second polarization filter.

2. The optoelectronic sensor according to claim 1, wherein the radiation-detecting semiconductor region is arranged laterally adjacent to the radiation-emitting semiconductor region.

3. The optoelectronic sensor according to claim 1, wherein the radiation-emitting semiconductor region and the radiation-detecting semiconductor region are arranged on a common carrier.

4. The optoelectronic sensor according to claim 1, wherein a distance between the radiation-emitting semiconductor region and the radiation-detecting semiconductor region is less than 150 µm.

5. The optoelectronic sensor according to claim 1, wherein the first polarization filter and/or the second polarization filter is an absorbing polarization filter.

6. The optoelectronic sensor according to claim 1, wherein the first polarization filter and/or the second polarization filter is a reflective polarization filter.

7. The optoelectronic sensor according to claim 1, wherein the radiation-emitting semiconductor region and the radiation-detecting semiconductor region are surrounded in a lateral direction by a plastic molding compound.

8. The optoelectronic sensor according to claim 1, wherein the first polarization filter and/or the second polarization filter are surrounded in a lateral direction by a plastic molding compound.

9. The optoelectronic sensor according to claim 7, wherein the plastic molding compound contains radiation-absorbing or radiation-reflecting particles.

10. The optoelectronic sensor according to claim 1, wherein the optoelectronic sensor is a surface mounted device.

11. The optoelectronic sensor according to claim 1, wherein the radiation-emitting semiconductor region is configured to emit infrared radiation and the radiation-detecting semiconductor region is configured to detect infrared radiation.

12. The optoelectronic sensor according to claim 1, wherein the optoelectronic sensor is configured to measure at least one vital parameter.

13. The optoelectronic sensor according to claim 1, wherein the optoelectronic sensor is a component of a wearable device.

14. The optoelectronic sensor according to claim 1, wherein the radiation-reflecting or radiation-absorbing layer directly adjoins the radiation-emitting semiconductor region, the radiation-detecting semiconductor region, the first polarization filter and the second polarization filter.

* * * * *